United States Patent
Canós et al.

(10) Patent No.: US 6,843,978 B2
(45) Date of Patent: Jan. 18, 2005

(54) MICROPOROUS MATERIALS (TIQ-6 AND METIQ-6) OF HIGH SURFACE AREA ACTIVE IN OXIDATION REACTIONS

(75) Inventors: Avelino Corma Canós, Valencia (ES); Vicente Fornes Segui, Valencia (ES); Urbano Díaz Morales, Valencia (ES); Marcelo Eduardo Domine, Valencia (ES)

(73) Assignees: Consejo Superior De Investigaciones Cientificas, Madrid (ES); Universidad Politecnica De Valencia, Valencia (ES)

( * ) Notice: Subject to any disclaimer, the term of this patent is extended or adjusted under 35 U.S.C. 154(b) by 15 days.

(21) Appl. No.: 10/155,564

(22) Filed: May 24, 2002

(65) Prior Publication Data

US 2002/0193239 A1 Dec. 19, 2002

Related U.S. Application Data

(63) Continuation of application No. PCT/ES00/00456, filed on Nov. 24, 2000.

(30) Foreign Application Priority Data

Nov. 24, 1999 (ES) .............................................. 9902655

(51) Int. Cl.$^7$ ................................................ C01B 39/06
(52) U.S. Cl. ............... 423/713; 423/326; 423/DIG. 23; 502/62; 562/118; 564/264; 568/300; 568/303; 568/420; 568/803
(58) Field of Search ................................ 423/713, 326, 423/DIG. 23; 502/62; 562/118; 564/264; 568/300, 303, 420, 803

(56) References Cited

U.S. PATENT DOCUMENTS

| | | | |
|---|---|---|---|
| 3,923,843 A | | 12/1975 | Wulff |
| 3,966,883 A | * | 6/1976 | Vaughan et al. ............. 423/712 |
| 4,016,245 A | * | 4/1977 | Plank et al. ................. 423/708 |
| 4,578,259 A | * | 3/1986 | Morimoto et al. .......... 423/703 |
| 4,975,258 A | * | 12/1990 | Barri .......................... 423/703 |
| 5,374,747 A | | 12/1994 | Saxton et al. |
| 6,469,226 B1 | * | 10/2002 | Chica Lara et al. ......... 585/739 |

FOREIGN PATENT DOCUMENTS

| | | |
|---|---|---|
| WO | WO 97/17290 | 5/1997 |
| WO | WO 00/34181 | 6/2000 |

OTHER PUBLICATIONS

Corma, A. et al., New aluminosilicate and titanosilicate delaminated materials active for acid catalysis and oxidation . . . J.AM. Chem. Sco. 2000, 122(12), pp 2804–2809, ISSN 0002–7863, Mar. 29, 2000.

Corma, A. et al., AlITQ–6: Synthesis, characterization and catalytic activity, Agnew–Chem. Int. Ed. 2000, 39 No 8, pp 1499–1501, ISSN 1433–7851.

Corma, A. et al., Strategies to improve the epoxidation activity and selectivity of TI–MCM–41, Chem. Commun. (Cambridge) 1998, (20), pp 2211–2212, Oct. 21, 1998.

Maschmeyer et al., Heterogeneous Catalysts Obtained by Grafting Metallocene Complexes onto Mesoporous Silica, Nature, 1995, Vo. 378.

* cited by examiner

Primary Examiner—David Sample
(74) Attorney, Agent, or Firm—Klauber & Jackson

(57) ABSTRACT

The present invention refers to a microporous material formed by oxygen, silicon, germanium, aluminum, boron, gallium, zirconium and/or titanium in its composition, called TIQ-6, to its catalytic applications in oxidation reactions, and to a method of the TIQ-6 material's preparation based on the synthesis of a gel with a titanium and/or zirconium content, its hydrothermal treatment under controlled conditions, and the treatment of the resulting laminar material with a solution of an organic compound containing a proton accepting group. This swollen material is subjected to a specific treatment to obtain a high external area delaminated solid. A material, METIQ-6, similar to the TIQ-6 material, but also having organic groups anchored on its surface incorporated by a post-synthesis process onto the TIQ-6 material is also claimed.

29 Claims, No Drawings

MICROPOROUS MATERIALS (TIQ-6 AND METIQ-6) OF HIGH SURFACE AREA ACTIVE IN OXIDATION REACTIONS

This is a continuation of Application No. PCT/ES00/00456, filed Nov. 24, 2000.

TECHNICAL FIELD OF THE INVENTION

The present invention is encompassed in the field of catalytic materials and, more specifically, in the field of zeolitic catalytic materials.

STATE OF THE ART PRIOR TO THE INVENTION

In the epoxidation of olefins methods are known in which organic hydroperoxides are utilised and which are carried out employing catalysts based on titanium anchored on siliceous supports (U.S. Pat. No. 3,923,843, 1975). An adequate selection of the reagent on titanium and also of the anchoring conditions permit catalysts to be obtained in which the titanium centres are separated and immobilised, reducing or rather cancelling the possibilities of deactivation of the catalyst through dimerisation of the titanium species. However, these catalysts can, during the catalytic process, suffer a loss of titanium content by extraction during the reaction which leads to the activity of the catalyst diminishing with time.

To overcome this drawback, it has been proposed that the titanium species be anchored on mesoporous silicas (T. Maschmeyer et. Al., Nature, 378, 159 (1995)). In this case, determined amounts of titanium of the order of 8% by weight can be anchored presenting good results as catalysts in epoxidation of olefins using organic peroxides as oxidising agents. Unfortunately the amorphous nature of these mesoporous silicas and the high concentration and proximity of silinol groups result in these materials being of low stability and to achieve adequate dispersions of the active titanium species on the surface of the mesoporous material proves to be problematic.

U.S. Pat. No. 4,975,258 discloses a crystalline material designated SUZ-2 having an empirical formula:

$$m(M_{2/a}O):X_{xz/2}:yYO_2$$

wherein m is 0.5 to 1.5; M is a cation of valency a; X is a metal of valency x, selected from Al, B, Ga, Zn, Fe and Ti; z is 2 when x is an odd number, and z is 1 when z is an even number, y is at least 5; and Y is silicon or Ge. Although it can partially coincide with the material of the present invention in the chemical composition of certain embodiments, the structure is different and therefore, the X-ray diffraction pattern is different.

U.S. Pat. No. 6,469,226 discloses a delaminated microporous solid, called ITQ-6, which has a similar chemical structure with the material of the present invention, but it has a different chemical composition.

Finally, CN-1113454 discloses a crystalline molecular sieve having a framework isomorphous with zeolite beta and containing Si and Ti, but essentially no framework Al, useful in the epoxidation of olefins with hydrogen peroxide as oxidant.

The methods and materials of the state of the art therefore suffer from a series of drawbacks that it would be convenient to overcome.

OBJECTS OF THE INVENTION

The object of the present invention is to overcome the drawbacks in the state of the art, by means of a catalyst and by means of a procedure for the preparation thereof, making use of a material with an external high surface area and which shows in its structure active species, as for example, titanium and/or zirconium in tetrahedral positions which have been incorporated directly during the synthesis without carrying out any post-synthesis anchoring treatment, the activity and selectivity obtained in oxidation reactions being very high.

Likewise, the present invention has a further object a modification of the surface area which gives rise to the formation of organic species bound to the surface which notably improve the activity and selectivity of these materials when they are used as catalysts.

DESCRIPTION OF THE INVENTION

The objects of the invention are achieved, on one hand, by means of a delaminated ferrierite zeolitic TIQ-6 material with a chemical composition corresponding to the formula, expressed as oxides, $SiO_2:zZO_2:mMO_2:xX_2O_3:aH_2O$ where Z is Ge, Sn z lies between 0 and 0.25 mol.mol$^{-1}$ M is Ti or Zr m has a value between 0.00001 and 0.25, preferably between 0.001 and 0.1, X is Al, Ga or B x has a value between 0 and 1, and a has a value between 0 and 2.

Moreover, the objects of the present invention also by means of a microporous METIQ-6 material with a chemical composition represented by the formula $$SiO_2:yR_pO_{2-P/2}:zZO_2:mMO_2:xX_2O_3:aH_2O$$

wherein R is selected between hydrogen, alkyl groups with 1 to 22 carbon atoms, aryl groups with 6 to 36 carbon atoms, polyaromatic groups with 6 to 36 carbon atoms, said groups being selected from among non-functionalised groups and functionalised groups with functional groups selected between acid, amino, thiol, sulphonic and tetra-alkyl ammonium groups, Y is Si, Ge, Sn or Ti, and is bound directly to atoms which compose a structure by means of C—Y bonds, p has a value between 1 and 3, y has a value between 0.0001 and 1, Z is Ge or Sn z lies between 0 and 0.25 mol.mol$^{-1}$ M is Ti or Zr m has a value between 0.00001 and 0.25, preferably between 0.001 and 0.1, X is Al, Ga or B, x has a value between 0 and 1, and a has a value between 0 and 2.

Preferably both the zeolitic TIQ-6 material and the microporous METIQ-6 material, can have a specific external surface area greater than 500 m$^2$g$^{-1}$, a pore volume greater than 0.5 cm$^3$g$^{-1}$, and a charge transfer band in the visible-ultraviolet spectrum in the range between 200 and 230 nm.

According to the invention, the TIQ-6 material may or may not be subsequently modified by means of a treatment with reagents selected among organogermanes, organosilanes, organometals and combinations thereof, in order to produce organic species anchored on the surface of the materials described, giving rise to the METIQ-6 material.

The TIQ-6 material can be obtained from laminar precursors of zeolites synthesised with titanium and/or zirconium which is incorporated directly into its structure. More specifically, a delaminated TIQ-6 material ia obtained, similar to the material ITQ-6, both proceeding from the laminar precursor of Ferrierite (FER), the preparation of which is indicated in the Spanish Patent P9801689 (1998) and in the patent application PCT/GB99/02567 (1999). The catalytic material obtained has Si—O—M bonds (M=Ti or Zr), the active species of titanium or zirconium being distributed in a homogeneous manner in order that they be functional in selective oxidation processes of organic compounds with organic or inorganic peroxides, and in general in processes which involve the use of Lewis acid centres.

Thus, in accordance with the invention, the TIQ-6 material can be prepared by means of a procedure which comprises A first step wherein a laminar precursor is synthesised of the ferrieritic type with a structure which comprises at least one of Ti and Zr;

A second step wherein the laminar precursor is submitted to a swelling with a long-chain organic compound, in order to obtain a swollen laminar material;

A third step wherein the swollen laminar material is, at least partially, delaminated using techniques of mechanical stirring, ultrasounds, spray drying, liophilisation and combinations thereof;

A fourth step wherein the at least partially delaminated material is subjected to an acid treatment;

A fifth step wherein the at least partially delaminated material is subjected to calcination until at least part of the organic matter present in the material is eliminated in order to obtain a calcinated material.

In this process, the laminar precursor can be prepared by means of a mixing step which comprises mixing, in an autoclave, a silica source, a titanium and/or zirconium source, a fluoride salt and acid, a structure director organic compound, and water until a mixture is obtained;

a heating step wherein the mixture is heated at autogenous pressure to between 100 and 200° C., preferably less than 200° C., with stirring, for 1 to 30 days, preferably between 2 and 15 days, until a synthesis material is obtained; and a final step wherein the synthesis material is filtered, washed and dried at a temperature less than 300° C. until the laminar precursor is obtained.

In the procedure described above, preferably use is made of a source of silica as pure as possible. Adequate silica sources are commercially available, for example under the trade names of AEROSIL (DEGUSSA AG), CAB-O-SIL (SCINTRAN BDH), LUDOX (DU PONT PRODUCTS); use can also be made of tetraethylorthosilicate (TEOS) and also combinations of various different sources of silica.

The titanium source can be selected among $TiCl_4$, tetraethylorthotitanate (TEOTi) and combinations thereof, and the zirconium is selected from between $ZrCl_4$, zirconyl chloride and combinations thereof.

As fluoride salt and acid, it is possible to use ammonium fluoride, hydrogen fluoride or combinations thereof.

The structure director organic compound is selected preferably between 1,4-diaminobutane, ethylendiamine, 1,4-dimethylpiperazine, 1,4-diaminocyclohexane, hexamethylen imine, pirrolidine, piridine and preferably 4-amino-2,2,6,6-tetramethylpiperidine and combinations thereof.

In accordance with the invention, the zeolitic METIQ-6 material can be obtained by means of a reaction with reagents selected among organogermanes, organosilanes, and organometals selected among organotitanium or organotin in order to produce organic species anchored on the surface of the materials described, at a reaction temperature between 0 and 400° C., preferably in gas phase between 50 and 200° C., of the TIQ-6 material, for so to produce organic species anchored on the surface of the materials described. Thus, for said reaction to produce organic species anchored on the surface an agent can be employed selected among $R_1R_2R_3(R')Y$, $R_1R_2(R')_2Y$, $R_1(R')_3Y$, $R_1R_2R_3Y$—NH—$YR_1R_2R_3$, and combinations thereof, wherein $R_1$, $R_2$ and $R_3$ are selected among hydrogen, alkyl groups with 1 to 22 carbon atoms, aryl groups with 6 to 36 carbon atoms, polyaromatic groups with 6 to 36 carbon atoms, said groups being selected between groups identical and different from each other, and selected in turn between non-functionalised groups and functionalised groups with functional groups selected among acid, amino, thiol, sulphonic and tetra-alkyl ammonium groups, R' is a hydrolysable group at a temperature between 0 and 400° C., selected from between alcoxide, halide, and trimethyllsililamino. Such halide groups can come from compounds like for example, methyltrichlorogermane, iodopropyltrimethoxysilane, titanocene dichloride, methyltrichlorotin, diethyldichlorosilane and methyl triethoxysilane. Such alcoxide groups can be for example ethoxide, methoxide, propoxide or butoxide. Such trimetthylsililamino groups can come from compounds like for example hexamethyldisilazane.

Y is at least one element selected from Si, Ge, Sn, Ti.

According to the invention, the reaction to produce organic species anchored on the surface can be carried out in the absence of solvents, but also by dissolving the TIQ-6 material in a solvent selected between organic solvents and inorganic solvents. Likewise the silanisation can be carried out in the absence of catalysts or in the presence of at least one catalyst which favours a reaction of an alkylsilane, alkylgermane or organometallic compound in general with Si— groups.

In accordance with the invention, the zeolitic material TIQ-6 may be prepared as follows: in a first step the synthesis of the laminar precursor is carried out by mixing in an autoclave a source of silica like for example AEROSIL, CAB-O-SIL, LUDOX, tetraethylorthosilicate (TEOS), or any other known; a source of titanium and/or zirconium like for example $TiCl_4$, tetraethylorthotitanate (TEOTi), $ZrCl_4$, zirconyl chloride or any other known; some fluoride compounds like for example ammonium fluoride and hydrogen fluoride; an organic compound like 1,4-diaminobutane, ethylendiamine, 1,4-dimethylpiperazine, 1,4-diaminocyclohexane, hexamethylenimine, pirrolidine, piridine and preferably 4-amino-2,2,6,6-tetramethylpiperidine and water in adequate proportions. The synthesis takes place at temperatures between 100 and 200° C., with constant stirring of the gel and lasting 1 to 30 days, preferably between 2 and 15 days. At the end of this time, the reaction product, a white solid, is washed with distilled water, filtered and dried.

The sheets of the obtained precursor, which contain titanium and/or zirconium in their framework, are separated by intercalating voluminous organic species such as alkyl ammoniums, amines, esters, alcohols, dimethylformamide, sulphoxides, urea, chlorohydrates of amines, alone or mixtures thereof in solution. The solvent is generally water, but other organic solvents can also be used such as alcohols, esters, alkanes, alone or mixtures thereof in absence or in presence of water.

More specifically, when cetyltrimethylammonium bromide ($CTMA^+Br^-$) is employed for example, as swelling agent, the intercalation conditions are as follows: the laminar precursor is dispersed in an aqueous solution of $CTMA^+Br^-$ and a tetra-alkyl ammonium hydroxide or an alkaline or alkaline-earth hydroxide, being preferred tetra-alkyl ammonium hydroxides like tetrapropylammonium hydroxide ($TPA^+OH^-$), the pH of the mixture being greater than 11. The resulting dispersion is heated to temperatures between 5 and 200° C. during periods between 0.5 and 90 hours whilst the suspension is vigorously stirred. The suspension resulting is dispersed in an excess of water, being stirred with a metal paddle of the Cowles type or any other known at speeds lying between 20 and 2000 rpm during periods not less than 1 hour. These conditions are sufficient to carry out the delamination of the precursor material. However, it is possible to employ other delamination methods such as for example treating the sample with ultrasounds, liophilisation and spray-drying.

Once the delamination has been carried out, the solids are separated and thoroughly washed in order to eliminate the excess $CTMA^+Br^-$. The obtained product is dried and is calcinated at a temperature sufficient to eliminate the organic matter occluded in the material, or at least the organic matter present on the material surface.

The materials obtained are characterised in that they have a high external surface area greater than 500 $m^2g^{-1}$ and a pore volume greater than 0.5 $cm^3g^{-1}$. They are likewise characterised in that they have a highly hydroxylated surface as may be deduced from the presence of a very intense band in the IR spectrum centered at about 3745 $cm^{-1}$. Moreover the ultraviolet-visible spectrum of the TIQ-6 materials which contain Ti or Zr are characterised by the presence of an $M^{IV}$-O charge transfer band between 200 and 220 nm.

This product containing Ti and/or Zr is active and selective in oxo-transference reactions and more specifically for epoxidation of olefins, oxidation of alkanes and alcohols, hydroxylation of aromatics, ammoximation of ketones, oxidation of organic sulphides and sulphoxides with organic or inorganic peroxides. Thus for example, the material termed TIQ-6 prepared from a laminar precursor of ferrieritic type, containing between 0.125 and 3% by weight of $TiO_2$ is capable of epoxidating the 1-hexene at 50° C. with conversions of 20% and selectivities to the epoxide of 96% after seven hours of reaction using hydrogen hydroperoxide ($H_2O_2$) as oxidant, acetonitryl and/or methanol as solvent and 2% by weight of TIQ-6 as catalyst.

On the other hand, to obtain the microporous METIQ-6 material from the zeolitic TIQ-6 material, the TIQ-6 material can be treated with reagents selected among organogermanes, organosilanes, and organometals selected among organotitanium or organotin. By means of this process to produce organic species anchored on the surface it is possible to add one or more groups which incorporate carbon-tetravalent element bonds in the zeolitic material. This reaction for incorporating these groups is carried out using compounds with formula $R_1R_2R_3(R')Y$, $R_1R_2(R')_2Y$, $R_1(R')_3Y$ or $R_1R_2R_3Y$—NH—$YR_1R_2R_3$ in which $R_1$, $R_2$ and $R_3$ are organic groups identical to or different from each other, and can be H or the alkyl or aryl groups mentioned earlier and Y is a metal among which Si, Ge, Sn or Ti are preferred. The procedures to produce organic species anchored on the surface are well known in the state of the art, in this manner the greater part of the Si-OH and M-OH groups present in the TIQ-6 material are functionalised.

The TIQ-6 and METIQ-6 materials can be employed as catalysts in the epoxidation of olefins, wherein an olefin, for example selected among propylene, ethylene, isoprene, norbornene, limonene, α-pinene, terpinolene, longifolene, cariofilene, c-cedrene, styrene, substituted stirenes, fatty esters and acids, allyl alcohols and vinyl alcohols, is subjected to epoxidation with an organic or inorganic hydroperoxide, as for example terabutylhydroperoxide, hydroperoxide of cumene or hydrogen peroxide;

oxidation of alcohols, in which an alcohol is subjected to oxidation with a hydroperoxide selected between organic hydroperoxides and inorganic hydroperoxides, in order to obtain a ketone, aldehyde or an acid from the alcohol;

oxidation of organic thiols to the corresponding sulphoxides and sulphons with a hydroperoxide selected between organic hydroperoxides and inorganic hydroperoxides;

hydroxylation of aromatic compounds with a hydroperoxide selected between organic hydroperoxides and inorganic hydroperoxides;

ammoximation of ketones with a hydroperoxide selected between organic hydroperoxides and inorganic hydroperoxides.

Thus for example, a METIQ-6 material containing between 0.125 and 3% by weight of $TiO_2$ is capable of epoxidating the 1-hexene at 50° C. with conversions of 18% and selectivities to the epoxide of 99% after seven hours of reaction using hydrogen hydroperoxide ($H_2O_2$) as oxidant, acetonitryl and/or methanol as solvent and 2% by weight of METIQ-6 as catalyst.

MODES OF EMBODIMENT OF THE INVENTION

The following examples illustrate characteristics applicable to the preparation of the TIQ-6 and METIQ-6 materials and of their applications as catalysts in oxidation processes.

EXAMPLE 1

Preparation of the Laminar Precursor of the TIQ-6 Material 10 g of silica (AEROSIL 200, Degussa) are added to an aqueous solution containing 9.2 g of ammonium fluoride ($NH_4F$, Aldrich 98% purity), 3.4 g of hydrofluoric acid (HF, 48.1% purity) 26 g. of 4-amino-2,2,6,6-tetramethylpiperidine (FLUKA, 98% purity), 0.8 g of titanium tetraethoxide (Alfa, 98% purity) and 20.2 g of deionised water (MilliQ Quality of Millipore). The synthesis gel pH is 9. This reactive mixture is vigorously stirred for two hours at room temperature before placing it into an autoclave at 135° C. for 10 days. The resulting solid is filtered, thoroughly washed with water to a pH close to 7 and dried at 60° C. for 12 hours. The obtained laminar precursor shows a Si/Ti ratio of 50 measured by chemical analysis.

EXAMPLE 2

Delamination of a Ferrieryytic Laminar Precursor for Obtaining the TIQ-6 Material 1 g of the laminar precursor described in example 1 is dispersed in a solution containing 4 g of MilliQ water, 20 g of cetyltrimethyl ammonium hydroxide and 6 g of tetrapropyl ammonium hydroxide, and the final pH is 12.5. These hydroxides were prepared by ion exchange of their respective bromide salts using DOWEX SBR resin. The bromide exchange level in both cases was approximately 70%.

The resulting dispersion was heated to 80° C. for 16 hours with constant, vigorous stirring to favour the separation of the sheets making up the precursor material. Once this time has elapsed, the resulting suspension is filtered to remove the excess of CTMA$^+$Br$^-$ and the solid is dispersed in an excess of water and subjected to an ultrasounds treatment for one hour. HCl is then added (6M) to pH=3 to favour the solid's flocculation. The latter is recovered by centrifuging and thoroughly washed with distilled water. The final solid is dried at 60° C. for 12 hours and roasted at 580° C. in a nitrogen atmosphere for 3 hours, the heat treatment being extended for 7 more hours in air, and all organic material hidden in the solid's pores is completely eliminated. The product gives a Si/Ti ratio of 100 measured by chemical analysis.

This material (TIQ-6) shows a specific area of approximately 650 m$^2$g$^{-1}$ and a pore volume of 0.7 cm$^3$g$^{-1}$.

EXAMPLE 3

Preparation of the METIQ-6 Material

Silanization of the TIQ-6 material, giving rise to the material called METIQ-6, is carried out by making organosilane compounds to react on the surface of a material like that described in example 2. This process is usually performed in the following manner: 3 g of the TIQ-6 material described in example 2 are dehydrated at 300° C. and vacuum of 10$^{-3}$ torr for 2 hours. A solution is added to this solid, containing 1.9 g of trimethylchlorosilane in 27 g of chloroform. The resulting suspension is vigorously shaken for 1 hour under an argon atmosphere, and then 1.28 g of triethylamine dissolved in 3 g of chloroform are added. This suspension is stirred for 1 hour at room temperature and is filtered, washed with dichloromethane and dried at 60° C. for 12 hours.

This material shows no significant nor structural nor textural differences with the TIQ-6 material described in example 2. The visible ultraviolet spectrum of this material shows a narrow band of 220 nm assigned to the formation of monomeric titanium species. The presence of Si—CH$_3$ groups is evidenced by the presence of a band in the IR spectrum at 1410 cm$^{-1}$ and a resonance line in the spectrum of $^{29}$Si-MAS-RMN at 15 ppm.

EXAMPLE 4

Catalytic Activity of the TIQ-6 Material Containing Ti in its Composition, in the 1-Hexene Epoxidation The catalytic activity of the material prepared in example 2 for 1-hexene epoxidation is described in this example.

300 mg of the material described in example 2 are placed into a glass reactor at 50° C. which contains 1420 mg of 1-hexene, 450 mg of H$_2$O$_2$ (at 35% P/P) and 11800 mg of acetonitryl or methanol as a solvent. The reaction mixture is stirred and a reaction sample is taken after 7 hours. Under these conditions, the conversion of 1-hexene achieved with respect to the maximum possible is 20% with a 96% epoxide selectivity.

EXAMPLE 5

Catalytic Activity of the TIQ-6 Material Containing Ti in its Composition, In 2-Norbornene Epoxidation The catalytic activity of the material prepared in example 2 for 2-norbornene epoxidation is described in this example.

300 mg of the material described in example 2 are placed into a glass reactor at 60° C. which contains 1550 mg of 2-norbornene, 500 mg of H$_2$O$_2$ (at 35% P/P) and 11800 mg of acetonitryl or methanol as a solvent. The reaction mixture is stirred and a reaction sample is taken after 7 hours. The conversion of 2-norbornene with respect to the maximum possible is 90% with a 94% epoxide selectivity.

EXAMPLE 6

Catalytic Activity of the TIQ-6 Material Containing Ti in its Composition, in Terpinolene Epoxidation The catalytic activity of the material prepared in example 2 for terpinolene epoxidation is described in this example.

300 mg of the material described in example 2 are placed into a glass reactor at 60° C. which contains 2200 mg of terpinolene, 500 mg of H$_2$O$_2$ (at 35% P/P) and 11800 mg of acetonitryl or methanol as a solvent. The reaction mixture is stirred and a reaction sample is taken after 7 hours. The conversion of terpinolene compared to the maximum possible is 46% with a 70% epoxide selectivity.

EXAMPLE 7

Catalytic Activity of the TIQ-6 Material Containing Ti in its Composition, in Cyclohexene Epoxidation The catalytic activity of the material prepared in example 2 for cyclohexene epoxidation is described in this example.

300 mg of the material described in example 2 are placed into a glass reactor at 60° C. which contains 4500 mg of cyclohexene and 1538 mg of tertbutylhydroperoxide. The reaction mixture is stirred and a reaction sample is taken after 5 hours. The conversion of cyclohexene with respect to the maximum possible is 81% with a 94% epoxide selectivity.

EXAMPLE 8

Catalytic Activity of the METIQ-6 Material Containing Ti in its Composition, in 1-Hexene Epoxidation The catalytic activity of the material prepared in example 3 for 1-hexene epoxidation is described in this example.

300 mg of the material described in example 3 are placed into a glass reactor at 50° C. which contains 1420 mg of 1-hexene, 450 mg of H$_2$O$_2$ (at 35% P/P) and 11800 mg of acetonitrile or methanol as a solvent. The reaction mixture is stirred and a reaction sample is taken after 7 hours. The conversion of 1-hexene with respect to the maximum possible is 18% with a 99% epoxide selectivity.

EXAMPLE 9

Catalytic Activity of the METIQ-6 Material Containing Ti in its Composition, in Cyclohexene Epoxidation The catalytic activity of the material prepared in example 3 for cyclohexene epoxidation is described in this example.

300 mg of the material described in example 2 are placed into a glass reactor at 60° C. which contains 4500 mg of cyclohexene and 1538 mg of tertbutylhydroperoxide. The reaction mixture is stirred and a reaction sample is taken after 5 hours. The conversion of cyclohexene with respect to the maximum possible is 88% with a 98% epoxide selectivity.

EXAMPLE 10

Catalytic Activity of the METIQ-6 Material Containing Ti in its Composition, in Terpinolene Epoxidation The catalytic activity of the material prepared in example 3 for terpinolene epoxidation is described in this example.

150 mg of the material described in example 3 are placed into a glass reactor at 60° C. which contains 1135 mg of cyclohexene and 1380 mg of tertbutylhydroperoxide. The reaction mixture is stirred and a reaction sample is taken after 7 hours. The conversion of terpinolene with respect to the maximum possible is 56% with a 78% epoxide selectivity.

What is claimed is:

1. A delaminated zeolitic material, TIQ-6 whose chemical composition corresponds to the formula, expressed as oxides, $$SiO_2:zZO_2:mMO_2:xX_2O_3:aH_2O$$

wherein
Z is Ge, Sn,
z is between 0 and 0.25 mol.mol$^{-1}$,
M is Ti or Zr,
m has a value between 0.00001 and 0.25,
X is Al, Ga or B,
x has a value between 0 and 1, and
a has a value between 0 and 2.

2. A delaminated zeolitic material according to claim 1, wherein the material has a specific external area higher than 500 m$^2$g$^{-1}$, a pore volume over 0.5 cm$^3$g$^{-1}$ and a load transfer band in the visible ultraviolet spectrum in the range between 200 and 230 nm.

3. A process for preparing the delaminated zeolitic TIQ-6 material of claim 1 or 2, comprising:
   a first step wherein a laminar precursor of ferrieritic type with a structure comprising at least one of Ti and Zr is synthesised;
   a second step wherein the laminar precursor is subjected to swelling with a long chain organic compound to obtain a swollen laminar material;
   a third step wherein the swollen laminar material is at least partially delaminated using mechanical stirring techniques, ultrasounds, spray drying, liophilisation and combinations thereof;
   a fourth step wherein the at least partially delaminated material is subjected to an acid treatment;
   a fifth step wherein the at least partially delaminated material is subjected to calcination until removing of at least part of the organic matter present in the material to obtain a calcinated material.

4. A process according to claim 3, wherein the acid treatment is carried out at a pH below 2.

5. A process according to claim 3 wherein the laminar precursor is prepared by
   a mixing step comprising mixing in an autoclave a silica source, a titanium and/or zirconium source, a salt and fluoride acid, a structure director organic compound and water until a mixture is obtained;
   a heating step wherein the mixture is heated at autogenous pressure, between 100 and 200° C., with stirring for 1 to 30 days until a synthesis material is obtained; and
   a final step wherein the synthesis material is filtered, washed and dried at a temperature below 300° C. until the laminar precursor is obtained.

6. A process according to claim 5, wherein the silica source is selected among sources of SiO$_2$, tetraethylorthosilicate (TEOS) and combinations thereof.

7. A process according to claim 5 wherein the titanium source is selected between TiCl$_4$, tetraethylorthotitanate (TEOTi) and combinations thereof.

8. A process according to claim 5, wherein the zirconium source is selected among ZrCl$_4$, zirconile chloride and combinations thereof.

9. A process according to claim 5, wherein the salt and fluoride acid are selected between ammonium fluoride, hydrogen fluoride and combinations thereof.

10. A process according to claim 5, wherein the structure director organic compound is selected among 1,4-diaminobutane, ethylenediamine, 1,4-dimethylpiperazine, 1,4-diaminocyclohexane, hexamethylenimine, pyrrolidine, pyridine, 4-amino-2,2,6,6-tetramethylpiperidine and combinations thereof.

11. A process according to claim 5, wherein the heating step lasts between 2 and 15 days.

12. A process according to claim 5, wherein the final step is carried out at a temperature below 200° C.

13. A method for the epoxidation of olefins, wherein an olefin is subjected to epoxidation with a hydroperoxide selected between organic and inorganic hydroperoxides, and the catalyst comprises a material according to either of claim 1 or 2.

14. A method according to claim 13, wherein the olefin is selected between propylene, ethylene, isoprene, norbonene, limonene, α-pinene, terpinolene, longifolene, cariofilene, α-cedrene, styrene, substituted styrenes, olefinic fatty esters and olefinic fatty acids, allylic alcohols and vinylic alcohols, and the hydroperoxides are selected among tertbutylhydroxiperoxides, cumene hydroperoxide and hydrogen peroxide.

15. A method for the oxidation of alcohols, wherein an alcohol is subjected to oxidation with a hydroperoxide selected between organic and inorganic hydroperoxides, and the catalyst comprises a material according to either of claim 1 or 2.

16. A method according to claim 15, wherein the alcohol is oxidized to ketone.

17. A method according to claim 15, wherein the alcohol is oxidated to aldehyde.

18. A method according to claim 15, wherein the alcohol is oxidized to acid.

19. A method for the oxidation of organic thiols to the corresponding sulphoxides and sulphons with a hydroperoxide selected between organic and inorganic hydroperoxides, and the catalyst comprises a material according to either of claim 1 or 2.

20. A method for the hydroxylation of aromatic compounds with a hydroperoxide selected between organic and inorganic hydroperoxides, and the catalyst comprises a material according to either of claim 1 or 2.

21. A microporous METIQ-6 material with a chemical composition represented by the formula $$SiO_2:yYR_pO_{2-p/2}:zZo_2:mMO_2:xX_2O_3:aH_2O$$

wherein
R is selected from the group consisting of hydrogen, alkyl groups with 1 to 22 carbon atoms, aryl groups with 6 to 36 carbon atoms, polyaromatic groups with 6 to 36 carbon atoms and these groups are selected among non functionalized groups and functionalized groups with functional groups selected from the group consisting of acid, amino, thiol, sulphonic and tetra-alkyl ammonium groups, Y is Si, Ge, Sn or Ti and is directly joined to atoms making up a structure by means of C—Y bonds, p has a value between 1 and 3, y has a value between 0.0001 and 1, Z is Ge or Sn, z has a value between 0 and 0.25 mol.mol$^{-1}$, M is Ti or Zr, m has a value between 0.00001 and 0.25, X is Al, Ga or B, x has a value between 0 and 1, and a has a value between 0 and 2.

22. A microporous material according to claim 21, wherein the material has a specific external area higher than 500 m$^2$g$^{-1}$, a pore volume over 0.5 cm$^3$g$^{-1}$ and a load transfer band in the visible ultraviolet spectrum in the range between 200 and 230 nm.

23. A method for preparing the microporous material according to claim 21, which comprises subjecting the zeolitic material to a reaction with reagents selected from the group consisting of organogermanes, organosilanes, organometals and combinations thereof, in order to generate organic species anchored on the surface of the described materials.

24. A method for preparing the METIQ-6 microporous material according to claim 21, which comprises subjecting the zeolitic material obtained to a process to produce organic species anchored on the surface, by means of a reaction with reagents selected among organogermanes, organosilanes and organometallics selected between organotitanium and organotin.

25. A method according to either of claims 23 and 24 wherein the material is subjected to a process to produce organic species anchored on the surface, at a reaction temperature between 0 and 400° C., using an agent selected between $R_1R_2R_3$ (R')Y, $R_1R_2(R')_2$Y, $R_1(R')_3$Y, $R_1R_2R_3$Y—NH—YR$_1$R$_2$R$_3$ and combinations thereof, wherein $R_1$, $R_2$ and $R_3$ are selected among hydrogen, alkyl groups with 1 to 22 carbon atoms, aryl groups with 6 to 36 carbon atoms, aromatic groups with 6 to 36 carbon atoms, polyaromatic groups with 6 to 36 carbon atoms and these groups are selected among identical groups and groups different to each other and selected, in turn, between non functionalised groups and groups functionalised with functional groups selected from the group consisting of acid, amino, thiol, sulphonic and tetra-alkyl ammonium groups, R' is a group hydrolysable at the reaction temperature, selected from the group consisting of alkoxide, halide and trimethylsilylamino groups Y is at least an element selected from the group consisting of Si, Ge, Sn, and Ti.

26. A method according to claim 25, wherein said process to produce organic species anchored on the surface is carried out by dissolving the material in a solvent selected between organic and inorganic solvents.

27. A method according to claim 25, wherein said process to produce organic species anchored on the surface is carried out in the presence of at least one catalyst which favours a reaction of an alkylsilane, alkylgermane or organometallic compound with Si— groups.

28. A method according to claim 23 wherein said process to produce organic species anchored on the surface is carried out in a gas phase and the reaction temperature is from 50 to 200° C.

29. A method for the ammoximation of ketones with a hydroperoxide selected between organic and inorganic hydroperoxides, and a catalyst comprising a material according to either of claim 1 or 21.

* * * * *